United States Patent
Williams

(10) Patent No.: US 8,247,534 B2
(45) Date of Patent: Aug. 21, 2012

(54) SYNTHESIS OF RADIOFLUORINATED PEPTIDE USING MICROWAVE ACTIVATION TECHNOLOGY

(75) Inventor: Lorenzo Williams, Olso (NO)

(73) Assignee: GE Healthcare AS, Oslo (NO)

( * ) Notice: Subject to any disclaimer, the term of this patent is extended or adjusted under 35 U.S.C. 154(b) by 335 days.

(21) Appl. No.: 12/517,561

(22) PCT Filed: Dec. 12, 2007

(86) PCT No.: PCT/NO2007/000439
§ 371 (c)(1),
(2), (4) Date: Jun. 4, 2009

(87) PCT Pub. No.: WO2008/072976
PCT Pub. Date: Jun. 19, 2008

(65) Prior Publication Data
US 2010/0016551 A1    Jan. 21, 2010

Related U.S. Application Data

(60) Provisional application No. 60/869,810, filed on Dec. 13, 2006.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. ...................................................... 530/335
(58) Field of Classification Search ....................... None
See application file for complete search history.

(56) References Cited

FOREIGN PATENT DOCUMENTS
WO   2004080492   9/2004
WO   2006030291   3/2006

OTHER PUBLICATIONS

Siro, et.al. "Easy Microwave Assisted Deprotection of N-Boc Derivatives" Synlett, 1998, pp. 147-148.
Bose, et.al. "An efficient and highly selective cleavage of N-tert-butoxycarbonyl group under microwave irradiation" Tetrahedron Letters, Elsevier, Amsterdam, vol. 39, No. 31, Jul. 30, 1998, pp. 5631-5634.
Kuznetsov, et.al. "Microwave activation in organic synthesis" Russian Journal of Organic Chemistry, Nauka/Interperiodica, MO, vol. 41, No. 12, Dec. 1, 2005, pp. 1719-1749.
Yngve, et.al., "Labelling of octreotide using 76Br-prosthetic groups" Journal of Labelled Compounds and Radiopharmaceuticals, vol. 44, No. 8, Jul. 2001, pp. 561-573.
Jauk, et.al. "Design and synthesis of a conformationally rigid mimic of the dihydropyrimidine calcium channel modulator SQ 32,926" Molecules 2000, vol. 5, pp. 227-239.
PCT/NO2007/000439 ISRWO dated Apr. 1, 2009.

*Primary Examiner* — Marcela M Cordero Garcia

(57) ABSTRACT

The present invention addresses a novel method of preparing radiofluorinated peptide-based compounds and introducing those compounds into an automated radiosynthesis apparatus with the aid of microwave activation. The present invention further relates to obtaining radiopharmaceutical kits utilizing microwave activation technology for the preparation of obtaining peptide based compounds as well as a method for the use of preparing a peptide based compound.

12 Claims, No Drawings

SYNTHESIS OF RADIOFLUORINATED PEPTIDE USING MICROWAVE ACTIVATION TECHNOLOGY

This application is a filing under 35 U.S.C. 371 of international application number PCT/NO2007/000439, filed Dec. 12, 2007, which claims priority to application No. 60/869,810 filed Dec. 13, 2006, in The United States the entire disclosure of which is hereby incorporated by reference.

FIELD OF THE INVENTION

The present invention addresses a novel method of preparing radiofluorinated peptide-based compounds and introducing those compounds into an automated radiosynthesis apparatus with the aid of microwave activation. The present invention further relates to obtaining radiopharmaceutical kits and a method for the use of to preparing a peptide based compound utilizing microwave activation technology.

BACKGROUND OF THE INVENTION

The application of radiolabelled bioactive peptides for diagnostic imaging is gaining importance in nuclear medicine. Biologically active molecules, which selectively interact with specific cell types, are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor-imaging studies. Therefore, $^{18}$F-labelled bioactive peptides have great clinical potential because of their utility in positron emission tomography (PET) to quantitatively detect and characterise a wide variety of diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins, which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO 03/006491 describes peptide-based compounds, which target integrin receptors associated with angiogenesis. International application PCT/GB2004/001052 describes methods suitable for labelling biologically active vectors with $^{18}$F and PCT/IB2005/002727 describes peptide-based compounds having utility for diagnostic imaging which may be prepared rapidly. One difficulty, however, remains is obtaining a stable and a more efficient method for synthesizing these peptide compounds in an automated radiosynthesis apparatus. The current invention sets forth herein that the use of microwave activation to improve the efficiency and reproducibility of peptide-based compounds that are utilized for PET imaging.

Discussion or citation of a reference herein shall not be construed as an admission that such reference is prior art to the present invention.

SUMMARY OF THE INVENTION

Peptide-based compounds allow for the incorporation of a Boc-protected aminoxy group, ie. a —O—NH—COOC(CH$_3$)$_3$ group, when used in an automated radiosynthesis apparatus. The corresponding compound with a free aminoxy terminus is unstable and it therefore would be beneficial to introduce it into an automated radiosynthesis apparatus in a protected form. Thereafter deprotection is performed and $^{18}$F is introduced into the target peptide compound. Both of these steps may be performed rapidly with the assistance of microwave technology such as microwave activation.

The automated radiosynthesis apparatus is designed to streamline PET radiopharmaceutical production. In general, an automated radiosynthesis apparatus features a single-use cassette system that accommodates different chemistries to facilitate the production of multiple PET tracers. PET imaging is limited by both the infrastructure and expertise required for producing radiopharmaceuticals. With the utilization of an automated radiosynthesis apparatus, all chemicals necessary to produce radiochemical PET imaging agents or tracers are preloaded in the exact quantities onto the single-use cassette. The user simply installs the cassette and pushes a button. Then, a cyclotron, which is an accelerator in which charged particles are propelled by an alternating electric field in a constant magnetic field, delivers an aqueous solution containing radioactive $^{18}$F-fluoride through a tube to the system. In a certain period, such as 23 minutes, the radiochemical PET imaging agent has been synthesized. The progress of the synthesis can be tracked on an accompanying computer. After synthesis, the program performs a rinsing cycle; after removing the cassette, the system is available for the next run.

In the current invention, the removal of the unstable Boc-protecting group located on peptide-based compounds can be done by irradiating the Boc-protected aminoxy precursor of the peptide-based compounds on a supported material cartridge and applying microwave activation. The microwave activation is e.g. for about 60 seconds to about 6 minutes and more preferably about 3 minutes. This form of deprotection leads to only gaseous byproducts being formed (isobutene and carbon dioxide), thus avoiding the use of acid and scavengers (e.g. trifloroacetic acid, thioanisole). No further workup is necessary. This transformation can be performed on a silica gel cartridge or other supported material (e.g. alumina, clays, graphite, $MnO_2$, Solid Phase Extraction cartridges). The final step to produce the radiolabelled compound is also performed on a supported material. Microwave activation would be utilized for this transformation as well.

The present invention further relates to radiopharmaceutical kits and the method for the use of manufacturing these kits to be used in an automated radiosynthesis apparatus with the aid of microwave activation. The present invention additionally depicts placing a reactor vessel inside a microwave reactor and introducing a magnetron into the reactor vessel thereby producing a microwave field generated by a magnetron. The present invention also presents a microwave oven, or preferably a monomodal microwave oven, connected through a reactor vessel to an automated radiosynthesis apparatus via an elongated tubing.

DETAILED DESCRIPTION OF THE INVENTION

The present invention addresses a novel method of introducing peptide-based compounds into an automated radiosynthesis apparatus with the aid of microwave activation. Peptide-based compounds allow for the incorporation of a Boc-protected aminoxy precursor when used in an automated radiosynthesis apparatus. The corresponding free aminoxy compound is unstable and it therefore would be beneficial to introduce it into an automated radiosynthesis apparatus in a protected form. Thereafter deprotection is performed and $^{18}$F, as a reporter, is introduced into the target peptide compound. Both of these steps may be performed rapidly with the assistance of microwave technology such as microwave activation.

The use of microwave activation substantially improves the efficiency and reproducibility of peptide-based compounds that are utilized for PET imaging.

Due to microwave activation, chemical reaction times are shortened substantially; i.e. the reaction is completed within 2 minutes and less. This is a clear improvement from previous reaction times. For example, a 10 minute shortage of the reaction time saves about 10% of the $^{18}$F activity. Furthermore, microwave activation also leads to an increased radiochemical yield in the range from about 10% to about 50%, which is due to increased selectivity.

Suitably, a microwave oven, preferably a monomodal microwave oven is used to carry out microwave activation. Here a reactor vessel is found inside the microwave oven which is connected to an automated radiosynthesis apparatus via elongated tubing. The tubing should be transparent to the microwave oven and does not have any bearing on the reaction. Specifically, the connection between the microwave oven and the automated radiosynthesis apparatus occurs between the microwave reactor and the cassettes of the automated radiosynthesis apparatus.

Microwave activation is carried out at various wavelengths. The wavelengths used were shorter than one meter and longer than one millimeter and the most preferred wavelength is about 10-15 centimeters. Suitable microwave activation times range from 20 seconds to 2 minutes, preferably from 30 seconds to 90 seconds, particularly preferably from 45 seconds to 60 seconds.

A temperature control of the reaction is advisable when temperature sensitive radiochemical imaging agents comprising peptides or proteins as targeting vectors, are employed in the method according to the invention. Duration of the microwave activation should be adjusted in such a way, that the temperature of the reaction mixture does not lead to the decomposition of the radiochemical imaging agents. If a radiochemical imaging agent used in the method herein is comprised of peptides or proteins, higher temperatures applied for a shorter time are generally more favorable than lower temperatures applied for a longer time period. Microwave activation can be carried out continuously or in several microwave activation cycles during the to course of the reaction.

Another available system designed for chemical synthesis that can be used herein as a microwave activation system is placing the reactor vessel inside a microwave reactor and introducing a magnetron into the reactor vessel thereby producing a microwave field generated by a magnetron. The reactor vessel is found inside a microwave reactor which is connected to an automated radiosynthesis apparatus via elongated tubing. The tubing should be transparent to the microwave reactor and does not have any bearing on the reaction. Specifically, the connection between the microwave reactor and the automated radiosynthesis apparatus occurs between the microwave reactor and the cassettes of the automated radiosynthesis apparatus.

In both of the aforementioned microwave activation systems the reaction vessel is also exposed to ultrasound or light of specific wavelengths in order to enable certain chemistries to be performed. In general, the wavelengths of the microwave should be shorter than one meter and longer than one millimeter, or more preferably a wavelength of about 10-15 centimeters. Additionally, by extending the length of tubing the wavelengths can be varied.

As mentioned previously the automated radiosynthesis apparatus described herein is designed to streamline PET radiopharmaceutical production. The automated radiosynthesis apparatus alone is unable to achieve high efficiency, reproducibility, and stability of peptide-based compounds that are utilized for PET imaging without the aid of microwave activation. However, by placing the reaction vessel in a microwave oven, or preferably a monomodal microwave oven, or inside a microwave reactor and then introducing a magnetron into the reactor vessel, the automated radiosynthesis apparatus makes it feasible to perform microwave chemistry activation. Thus, by attaching a microwave reactor to an automated radiosynthesis apparatus would not change any hardware of the apparatus.

The magnetron disclosed herein is a diode-type electron tube which is used to produce 2450 MegaHertz of microwave energy. The magnetron is classed as a diode because it has no grid as does an ordinary electron tube. A magnetic field imposed on the space between the anode (plate) and the cathode serves as the grid. While the external configurations of different magnetrons will vary, the basic internal structures are the same.

Furthermore, there are various advantages of preparing for use in systems with the aid of microwave activation. The gaseous byproducts (isobutene and carbon dioxide) and microwave activation drive the chemical reaction of preparing $^{18}$F-peptide-based compounds to rapid completion. A further advantage of using microwave chemistry in the automated radiosynthesis apparatus is that the Boc-aminoxy derivative becomes stable.

One embodiment of the present invention encompasses preparing a method of preparing a radiofluorinated compound comprising the steps;

(i) for a compound of formula (I)

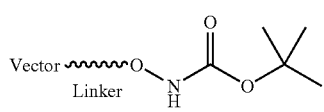
(I)

wherein the Boc-protecting group of (I) is removed by irradiating the Boc-protected aminoxy group on a supported material with microwave activation to give a compound of formula (II);

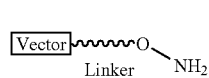
(II)

(ii) the compound (II) is reacted with a $^{18}$F-fluoride synthon to prepare the compound of formula (III)

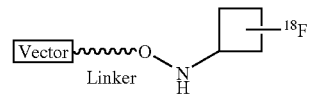
(III)

wherein step (ii) is also performed on a supported material with microwave activation.

As indicated above, the linker group in the compounds of formulas (I), (II), and (III) are attached to the Boc-group via an aminoxy-group (—ONH—), i.e. the Boc-protected aminoxy group is: —ONH—COO—C(CH$_3$)$_3$. The Boc-protecting groups is —COO—C(CH$_3$)$_3$.

The linker group in the compounds of formulae (I), (II), and (III) may be chosen to provide good in vivo pharmacokinetics, such as favourable excretion characteristics in the resultant end product. The term linker as used herein means a moiety that links together at least two other moieties, such as a vector and a reporter. The use of linker groups with different lipophilicities and or charge can significantly change the in vivo pharmacokinetics of the vector, such as a peptide to suit the diagnostic need. For example, where it is desirable for a conjugate of formula (IV) to be cleared from the body by renal excretion, a hydrophilic linker is used, and where it is desirable for clearance to be by hepatobiliary excretion a hydrophobic linked is used. A wide variety of linker may be used, including biodegradable linkers and biopolymers. The linker is at its simplest a bond between the vector and the aminoxy group. More generally, the linker will provide a mono- or multi-molecular skeleton, e.g. a linear, cyclic, or branched skeleton. The linker may further have the role to distance the vector from the reporter. The linker may comprise amino acids, or elements of such. Further, the linker may include structural type polysaccharides, storage-type polysaccharides, polyamino acids and methyl and ethyl esters thereof, and polypeptides, oligosaccharides and oligonucleotides. The linker may also comprise macromolecular structures such as dextran and preferably poly(ethyleneglycols), referred to as PEGs. Linkers including a PEG moiety have been found to slow blood clearance which is desirable in some circumstances. The linker may be derived from glutaric and/or succinic acid and/or a polyethyleneglycol based moiety.

A further embodiment of the present invention depicts a method pertaining to formulas (I), (II), and (III) wherein the vector is a peptide based vector. Yet another embodiment of the present invention shows a method pertaining to formulaes (I), (II), and (III) wherein a peptidic vector is an RGD-based peptide having affinity for angiogenesis. Additionally, a method pertaining to formulaes (I), (II), and (III) wherein the linker is based on a PEG building block is also claimed as a preferred embodiment of the present invention.

Still another embodiment of the present invention shows a method wherein compound of formula (I) is of formula (IV)

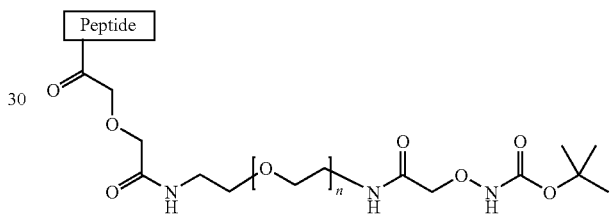
(IV)

wherein n=3-5 and n is preferably 5.

The reporter including a $^{18}$F-fluoride is introduced in step (ii) by reacting the compound of formula (II) with a $^{18}$F-fluoride synthon. This synthon may be illustrated as

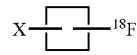

wherein X is a leaving groups e.g. selected from the group of ARCHO, AlkCHO, Arhal, ArOTs, AlkOMs, ArOTs. Examples of relevant $^{18}$F-fluoride synthons are provided in WO2004/080492, which is incorporated by reference. A preferred $^{18}$F-fluoride synthon is 4-$^{18}$F-radiolabelled benzaldehyde. Another embodiment of the present invention hence provides a method wherein the $^{18}$F-fluoride synthon is 4-$^{18}$F-radiolabelled benzaldehyde.

The present invention provides a more chemoselective approach to radiolabelling where the exact site of introduction of the label is pre-selected during the synthesis of the peptide or vector precursor. The ligation reaction occurring at a pre-determined site in the molecule and gives only a single labeled product. This methodology is therefore chemoselective, and its application is considered generic for labeling a wide range of drug-like molecules, peptides biomolecules such as small proteins.

Another embodiment of the present invention presents a method for preparing a compound of formula (V) based on formulas (I), (II), and (III)

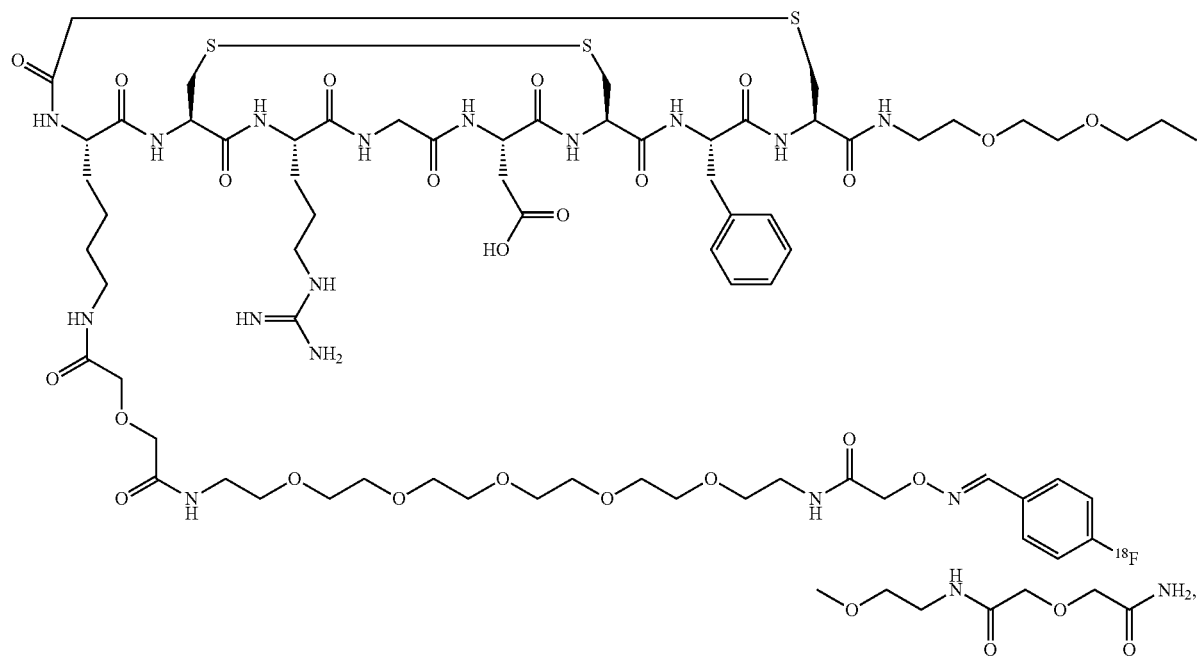

SEQ ID NO: 1.

Yet another embodiment of the present invention depicts a method based on formuleas (I), (II), and (III) where the supported material is silica gel, $SiO_2$, alumina, clay, graphite, $MnO_2$, or solid phase extraction cartridges.

Still a further embodiment depicts a method pertaining to formulaes (I), (II), and (III) wherein the supported material is silica gel.

A further embodiment shows a method for preparing a compound of formula (III) using microwave activation, wherein microwave activation is carried out by a microwave activation system further wherein a reactor vessel is found inside a microwave oven which is connected to an automated radiosynthesis apparatus via elongated tubing Still another embodiment shows a method for preparing a compound of formula (III) using microwave activation, wherein a reactor vessel is found preferably inside a monomodal microwave oven. Yet another embodiment of the invention embodies a method for the use of preparing a compound of formula (III) using microwave activation wherein microwave activation is carried out at wavelengths shorter than one meter and longer than one millimeter, preferably at a wavelength about 10-15 centimeters.

A further embodiment of the present invention depicts a radiopharmaceutical kit using microwave activation for preparing a compound of formula (III).

A vector used herein is a fragment of a compound or moiety having affinity for a receptor molecule, preferably a peptidic species or more preferably an angiogenesis targeting species such as an RGD peptide. A specific example of a vector used herein is an Arg-Gly-Asp peptide or an analogue thereof. An example of such a vector used herein comprises the fragment

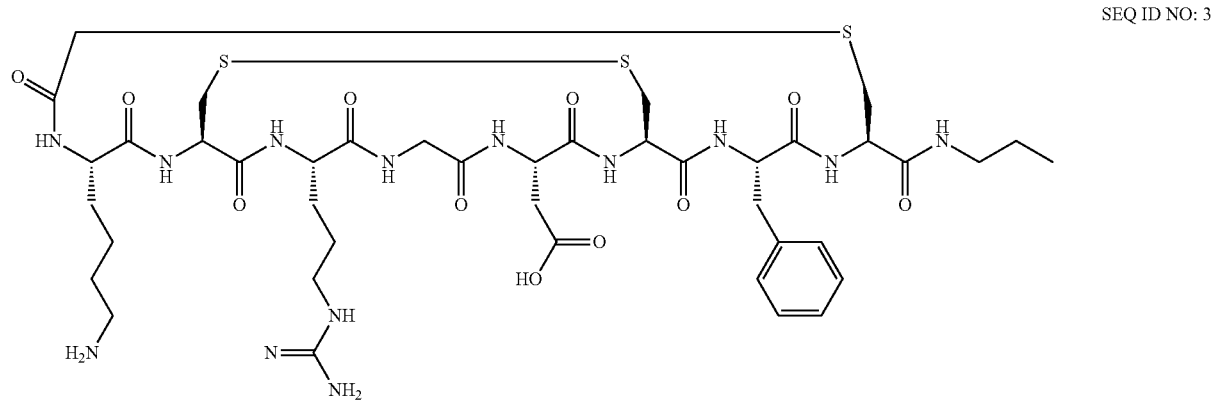

SEQ ID NO: 3

-continued

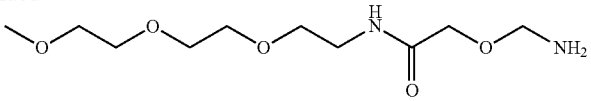

wherein a linker would be attached to the lysine amino group and said linker could be:

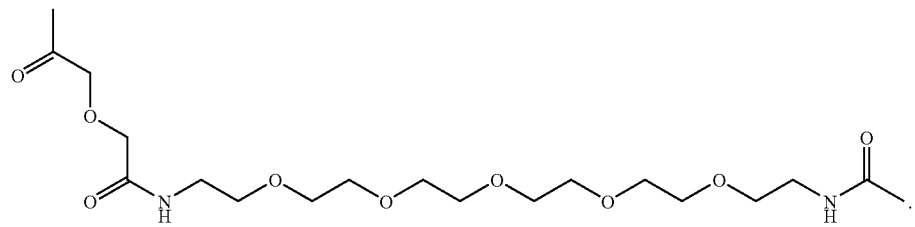

EXAMPLES

The invention is further described in the following examples, which is in no way intended to limit the scope of the invention.

The invention is illustrated by way of examples in which the following abbreviations are used:

| | |
|---|---|
| HPLC: | high performance liquid chromatography |
| NMR: | nuclear magnetic resonance |
| TFA: | trifluoroacetic acid. |
| hr(s): | hour(s) |
| min(s): | minute(s) |
| DMAP: | 4-(dimethylamino)pyridine |
| THF: | tetrahydrofuran |
| DCM: | dichloromethane |
| DMF: | N,N-dimethylformamide |
| TBAF: | tetrabutylammonium fluoride |
| MeOH: | methanol |
| TLC: | thin layer chromatography |
| TIS: | triisopropylsilane |
| DMSO: | dimethylsulphoxide |
| PBS: | phosphate buffered saline |
| PyAOP: | [7-azabenzotriazol-1-yloxytris(pyrrolidino)phosphonium-hexafluorophosphate] |
| Boc: | —COOCH($CH_3$)$_3$ |
| RT: | room temperature |
| SPE: | solid phase extraction |
| $CO_2$ (g): | carbon dioxide (gas) |
| $SiO_2$: | silica |
| $CH_2C(CH_3)_2$: | isobutene |

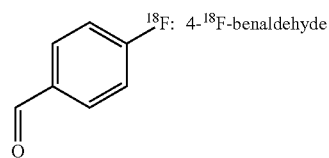

Removal of the Boc-Protecting Group with the Aid of Microwave Activation in Preparing a Radiolabeled Peptide-Based Compound The Boc-protecting group was removed by irradiating 0.1 millimoles of Boc-protected aminoxy precursor that was absorbed onto a silica gel cartridge at a frequency of about 2450 MegaHertz for about 3 minutes. This form for deprotection led to only gaseous byproducts being formed (isobutene and carbon dioxide), thus avoiding the use of acid and scavengers (e.g. trifluoroylacetic acid, thioanisole). The free amine can then be coupled to the radiolabelled moiety, either via only an automated radiosynthesis apparatus or in combination with a microwave activation system. In the latter case the final step was performed on a silica gel cartridge by adding 4-$^{18}$F-benzaldehyde to the aminoxy substrate. Microwave irradiation ensured mixing of all reactants via diffusion and also facilitated in driving the reaction to completion.

Due to microwave activation, chemical reaction times are shortened substantially; i.e. the reaction is completed within 2 minutes and less. This is a clear improvement from previous reaction times. For example, a 10 minute shortage of the reaction time saves about 10% of the $^{18}$F activity. Furthermore, microwave activation also leads to an increased radiochemical yield in the range from about 10% to about 50%, which is due to increased selectivity.

A microwave oven, specifically a monomodal microwave oven was used to carry out microwave activation. Microwave activation was carried out continuously and in several microwave activation cycles during the course of the reactions undertaken. Microwave activation was carried out at various wavelengths. The wavelengths used were shorter than one meter and longer than one millimeter and the most preferred wavelength was about 10-15 centimeters. The time it took for the microwave activation to complete one cycle occurred between 20 seconds to 2 minutes, with the best radiochemical yield of $^{18}$F activity being achieved between about 45 seconds to about 60 seconds.

A temperature control of irradiating the Boc-protected aminoxy precursor to obtain a peptide-based compound was utilized since temperature sensitive radiochemical imaging agents comprising peptides or proteins as targeting vectors, are employed in the method according to the present invention. The radiochemical imaging agent used in the method herein showed higher temperatures applied for a shorter time were generally more favorable than lower temperatures applied for a longer time period.

The following is an example of the synthesis for obtaining a radiofluorinated compound using a microwave activation system according to the invention:

11          12
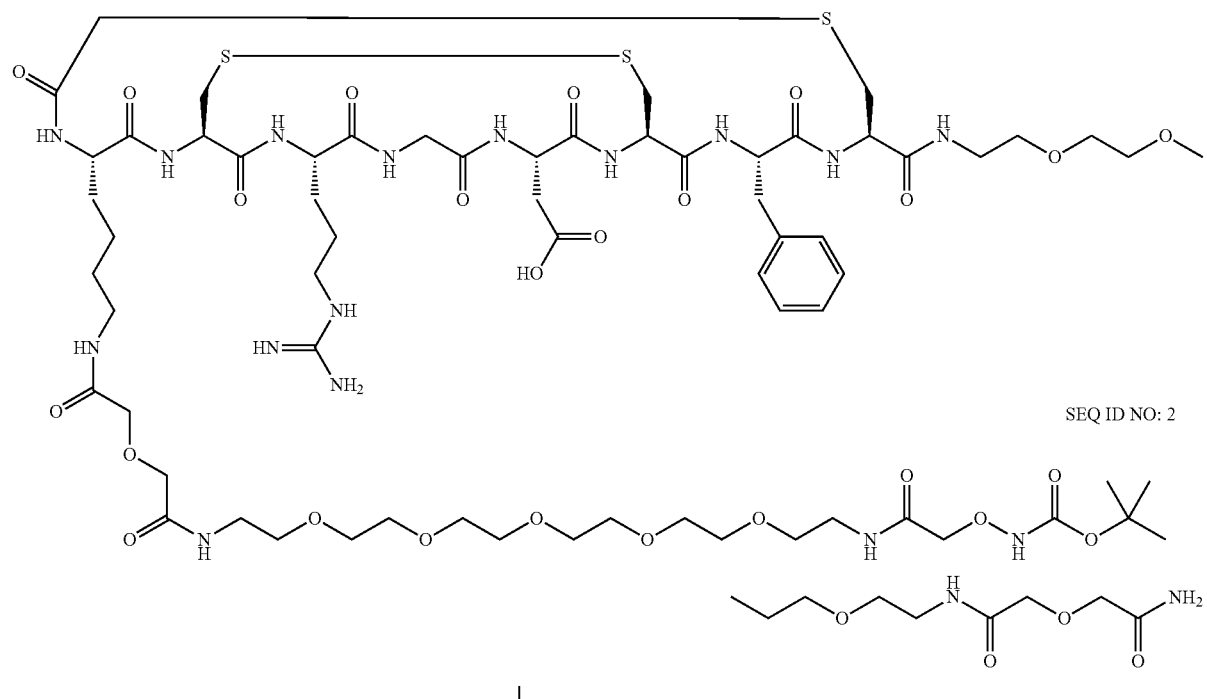
SEQ ID NO: 2
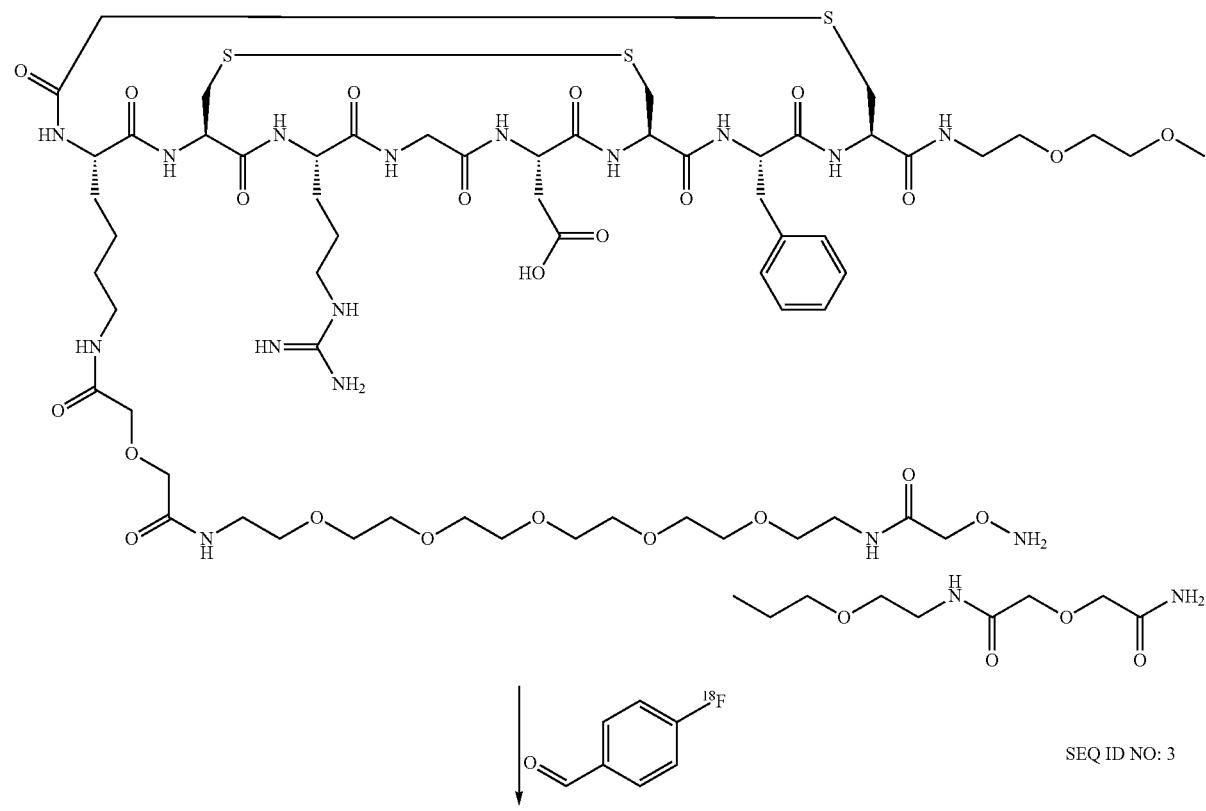
SEQ ID NO: 3

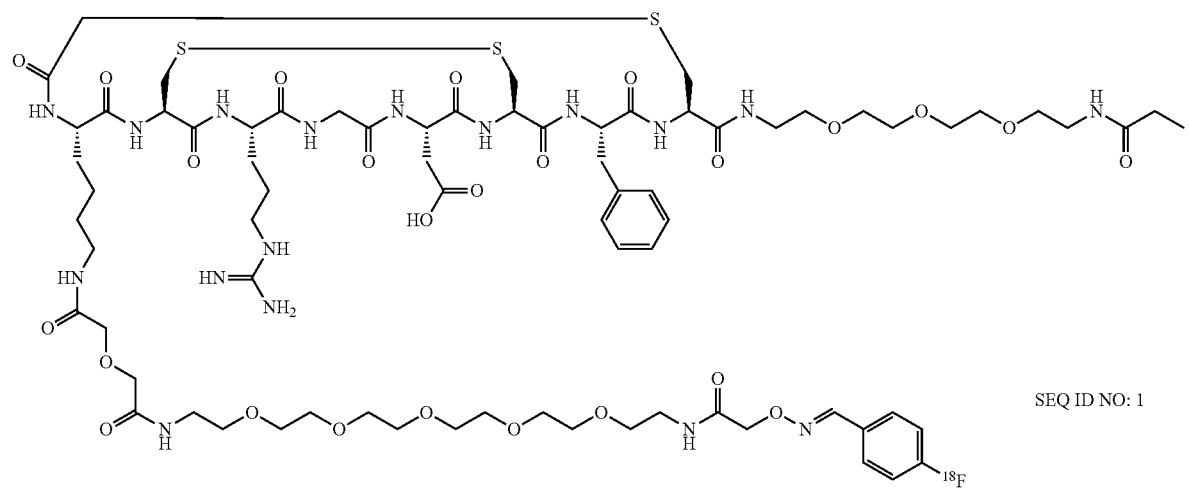
SEQ ID NO: 1
Preparation of a Peptide Precursor (Compound 1)
The peptide, compound 1 was synthesized using standard peptide synthesis.
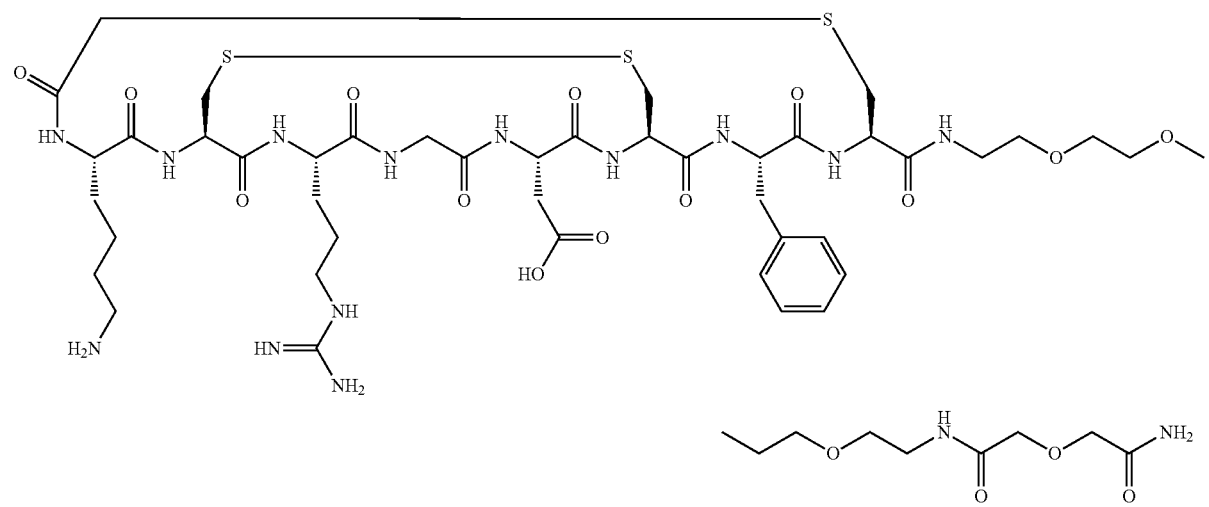
SEQ ID NO: 4
1

-continued

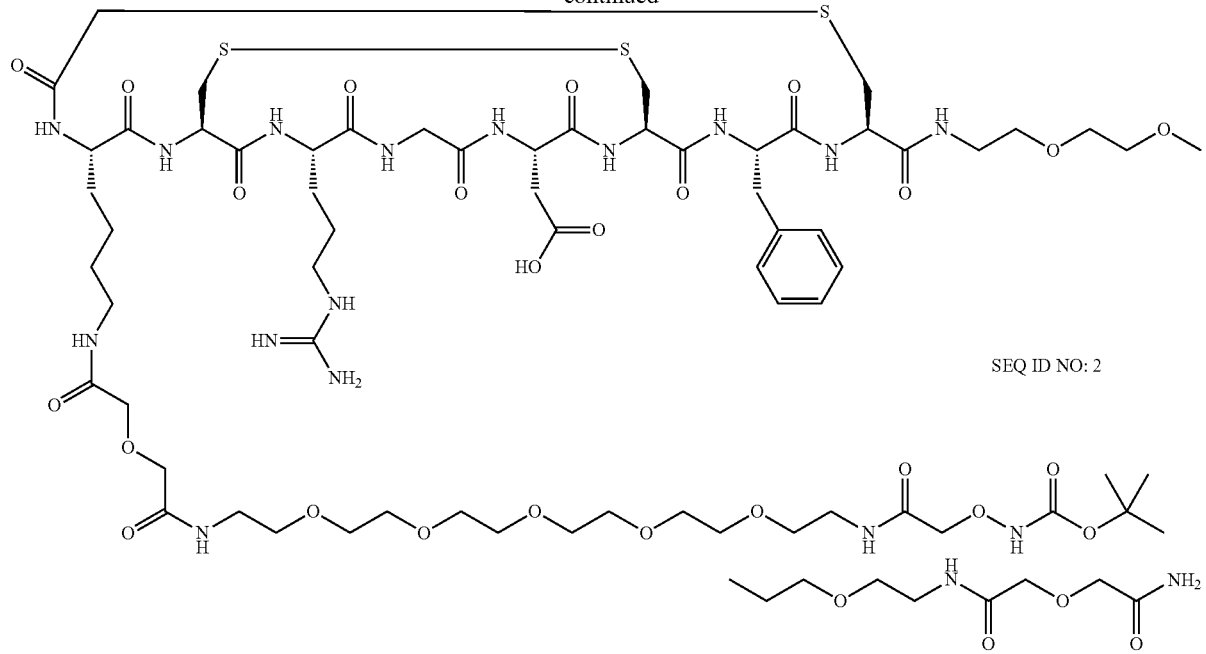

SEQ ID NO: 2

2

(a) 1,17-Diazido-3,6,9,12,15-pentaoxaheptadecane

A solution of dry hexaethylene glycol (25 g, 88 mmol) and methanesulphonyl chloride (22.3 g, 195 mmol) in dry THF (125 mL) was kept under argon and cooled to 0° C. in an ice/water bath. A solution of triethylamine (19.7 g, 195 mmol) in dry THF (25 mL) was added dropwise over 45 min. After 1 hr the cooling bath was removed and the reaction was stirred for another for 4 hrs. Water (55 mL) was then added to the mixture, followed by sodium hydrogencarbonate (5.3 g, to pH 8) and sodium azide (12.7 g, 195 mmol). THF was removed by distillation and the aqueous solution was refluxed for 24 h (two layers were formed). The mixture was cooled, ether (100 mL) was added and the aqueous phase was saturated with sodium chloride. The phases were separated and the aqueous phase was extracted with ether (4×50 mL). The combined organic phases were washed with brine (2×50 mL) and dried (MgSO$_4$). Filtration and evaporation of the solvent gave 26 g (89%) of a yellow oil. The product was used in the next step without further purification.

(b) 17-Azido-3,6,9,12,15-pentaoxaheptadecanamine

To a vigorously stirred suspension of 1,17-diazido-3,6,9,12,15-pentaoxaheptadecane (25 g, 75 mmol) in 5% HCl (200 mL) was added a solution of triphenylphosphine (19.2 g, 73 mmol) in ether (150 mL) over 3 hrs at room temperature. The reaction mixture was stirred for additional 24 hrs. The phases were separated and the aqueous phase was extracted with dichloromethane (3×40 mL). The aqueous phase was cooled in an ice/water bath and the pH was adjusted to 12 by addition of solid potassium hydroxide. The aqueous phase was concentrated and the product was taken up in dichloromethane (150 mL). The organic phase was dried (Na$_2$SO$_4$) and concentrated giving of 22 g (95%) of a yellow oil. The product was identified by electrospray mass spectrometry (ESI-MS) (MH$^+$ calculated: 307.19. found 307.4). The crude oil was used in the nest step without further purification.

(c) 23-Azido-5-oxo-6-aza-3,9,12,15,18,21-hexaoxatricosanoic acid

To a solution of 17-azido-3,6,9,12,15-pentaoxaheptadecanamine (15 g, 50 mmol) in dichloromethane (100 mL) was added diglycolic anhydride (Acros, 6.4 g, 55 mmol). The reaction mixture was stirred overnight. The reaction was monitored by ESI-MS analysis, and more reagents were added to drive the reaction to completion. The solution was concentrated to give a yellow residue which was dissolved in water (250 mL). The product was isolated from the aqueous phase by continuous extraction with dichloromethane over night. Drying and evaporation of the solvent gave a yield of 18 g (85%). The product was characterized by ESI-MS analysis (MH$^+$ calculated: 423.20. found 423.4). The product was used in the next step without further purification.

(d) 23-Amino-5-oxo-6-aza-3,9,12,15,18,21-hexaoxatricosanoic acid

23-Azido-5-oxo-6-aza-3,9,12,15,18,21-hexaoxatricosanoic acid (9.0 g, 21 mmol) was dissolved in water (50 mL) and reduced using H$_2$(g)-Pd/C (10%). The reaction was run until ESI-MS analysis showed complete conversion to the desired product (MH$^+$ calculated: 397.2. found 397.6). The crude product was used in the next step without further purification.

(e) (Boc-aminooxy)acetyl-PEG(6)-diglycolic acid

A solution of dicyclohexycarbodiimide (515 mg, 2.50 mmol) in dioxan (2.5 mL) was added dropwise to a solution of (Boc-aminooxy)acetic acid (477 mg, 2.50 mmol) and N-hydroxysuccinimide (287 mg, 2.50 mmol) in dioxan (2.5 mL). The reaction was stirred at RT for 1 h and filtered. The filtrate was transferred to a reaction vessel containing a solution of 23-amino-5-oxo-6-aza-3,9,12,15,18,21-hexaoxatricosanoic acid (1.0 g, 2.5 mmol) and N-methymorpholine (278 μl, 2.50 mmol) in water (5 mL). The mixture was stirred at RT for 30 min. ESI-MS analysis showed complete conversion to the desired product (MH+ calculated: 570.28. found 570.6).

The crude product was purified by preparative HPLC (column: Phenomenex Luna 5μ C18 (2) 250×21.20 mm, detection: 214 nm, gradient: 0-50% B over 60 min where A=H$_2$O/0.1% TFA and B=acetonitrile/0.1% TFA, flow rate: 10 mL/min) affording 500 mg (38%) of pure product.

TFA was replaced by HCOOH (gradient: 0-30% B, otherwise same conditions as above) afforded 89 mg (50%). The product was analysed by HPLC (column: Phenomenex Luna 3μ C18 (2) 50×2 mm, detection: UV 214 nm, gradient: 0-30% B over 10 min where A=H$_2$O/0.1% HCOOH and B=acetonitrile/0.1% HCOOH, flow rate: 0.3 mL/min, Rt: 10.21 min). Further product characterisation was carried out using ESI-MS (MH$_2^{2+}$ calculated: 905.4. found: 906.0).

Chemoselective Ligation of $^{18}$F-fluorobenzaldehyde to Compound 2 to give Compound 3

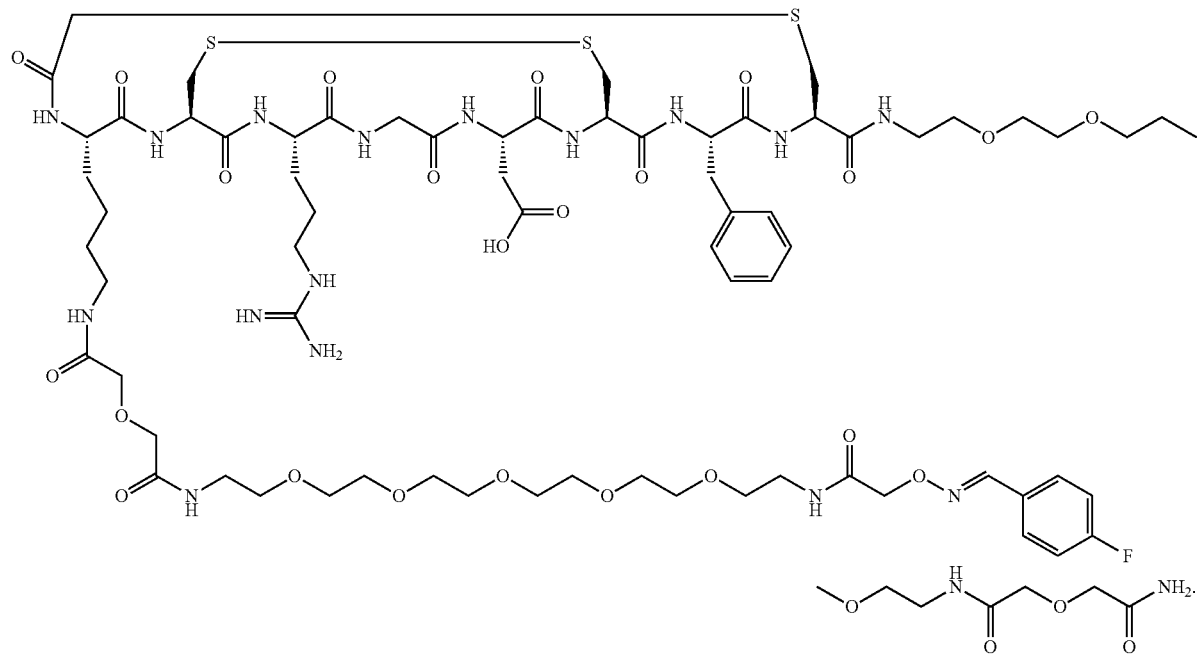

SEQ ID NO: 1

The product was analyzed by HPLC (column: Phenomenex Luna 3μ C18 (2), 50×2.00 mm, detection: 214 nm, gradient: 0-50% B over 10 min where A=H$_2$O/0.1% TFA and B=acetonitrile/0.1% TFA, flow rate: 0.75 mL/min, Rt=5.52 min). Further confirmation was carried out by NMR analysis.

(f) Conjugation of (Boc-aminooxy)acetyl-PEG(6)-diglycolic acid to Compound 1

(Boc-aminooxy)acetyl-PEG (6)-diglycolic acid (0.15 mmol, 85 mg) and PyAOP (0.13 mmol, 68 mg) were dissolved in DMF (2 mL). N-methylmorpholine (0.20 mmol, 20 μL) was added and the mixture was stirred for 10 min. A solution of Compound 2 (0.100 mmol, 126 mg) and N-methylmorpholine (0.20 mmol, 20 μL) in DMF (4 mL) was added and the reaction mixture was stirred for 25 min. Additional N-methylmorpholine (0.20 mmol, 20 μL) was added and the mixture was stirred for another 15 min. DMF was evaporated in vacuo and the product was taken up in 10% acetonitrile-water and purified by preparative HPLC (column: Phenomenex Luna 5μ C18 (2) 250×21.20 mm, detection: UV 214 nm, gradient: 5-50% B over 40 min where A=H$_2$O/0.1% TFA and B=acetonitrile/0.1% TFA, flow rate: 10 mL/min) affording 100 mg semi-pure product. A second purification step where Deprotection of peptide 2 was carried out by addition of TFA containing 5% water to 10 mg of peptide. The Boc-deprotected peptide (5.9 mg, 0.0044 mmol) in 1 ml water was added to 4-fluoro benzaldehyde (Compound 1) (1.1 mg, 0.94 μl, 0.0089 mmol) in 1 ml acetonitrile. pH of the mixture was 3.5. After 45 minutes at 70 degrees the mixture was purified by reverse phase preparative chromatography twice (Phenomenex Luna C18 column, 00G-4253-N0; solvents: A=water+0.1% TFA/B=CH$_3$CN+0.1% TFA, gradient: 10-40% B over 30 min; flow 5.0 ml/minute; detected at 214 nm), affording 2.0 mg (32%) of pure compound (analytical HPLC: Phenomenex Luna C18 column, 00G-4252-E0; solvents: A=water+0.1% TFA/B=CH$_3$CN+0.1% TFA, gradient: 10-50% B over 20 min; flow 1.0 ml lminute; retention time 16.3 minutes, detected at 214 and 254 nm). Further characterisation was carried out using mass spectrometry, giving m/z value 1437.2. [M-H+].

Radiosynthesis of 4 $^{18}$F-Compound

Method 1

$^{18}$F-fluoride (up to 370 MBq) was azeotropically dried in the presence of Kryptofix 222 (5 mg in 0.5 ml acetonitrile) and potassium carbonate (50 μl 0.1M solution in water) by heating under N$_2$ to 110° C. for 20 mins. During this time 3×0.5 ml acetonitrile were added and evaporated. After cooling to <40° C., a solution of trimethylammonium benzaldehyde triflate (1 mg in 0.4 ml DMSO) was added. The reaction vessel was sealed and heated to 90° C. for 15 mins to effect labelling. Meanwhile, Compound 3 (6 mg) was treated with 5% water in TFA (200 μl) for 5 mins at RT. The solvents were then removed in vacuo. The deprotected peptide was redissolved in 0.1M NH$_4$OAc buffer, pH4 (0.4 ml) and combined with 4-$^{18}$F-fluorobenzaldehyde in the reaction vessel. The reaction vessel was sealed and heated to 70° C. for 15 mins to effect conjugation. After cooling to room temperature, the product was obtained by preparative radio HPLC (column Phenomenex Luna C18(2) 5 μm 10×100 mm, solvents: A=water/0.1% TFA and B=acetonitrile/0.1% TFA; gradient 15-25% B over 5 min; 25% B for 12 mins; 25-50% B over 10 mins; flow 4.0 ml/min, UV detection at 210 and 254 nm). The product fraction was diluted with water (10 ml) and loaded onto a SepPak C18-plus cartridge (conditioned with 10 ml EtOH and 20 ml H$_2$O). Compound 4 was eluted in ethanol (1 ml). The ethanol was removed in vacuo and compound 4 was formulated in PBS.

Method 2 a) Radiosynthesis of $^{18}$F-fluorobenzaldehyde $^{18}$F-Fluoride (up to 370 MBq) is azeotropically dried in the presence of Kryptofix 222 (5 mg in 0.5 ml acetonitrile) and potassium carbonate (50 μl 0.1 M solution in water) by heating under N$_2$ to 110° C. for 20 mins. During this time 3×0.5 ml acetonitrile are added and evaporated. After cooling to <40° C., a solution of trimethylammonium benzaldehyde triflate (1 mg in 0.4 ml DMSO) is added. The reaction vessel is sealed and heated to 90° C. for 15 mins to effect labelling. The crude reaction mixture is cooled to room temperature and diluted by addition of water. The mixture will be passed sequentially through ion exchange cartridges (preconditioned with ethanol (or acetonitrile) and water) and eluted in an acetonitrile/water mixture. The eluate will be concentrated using a C18 Seppak, and the fluorobenzaldehyde will be eluted in acetonitrile.

b) Conjugation of Compound 2 and 3-$^{18}$F-fluorobenzaldehyde

Compound 2 is treated with 5% water in TFA for 5 mins at room temperature. The solvents are then removed by evaporation under vacuum. The peptide is redissolved in 0.1M NH$_4$OAc buffer, pH4 (0.5 ml) and combined with 4-$^{18}$F-fluorobenzaldehyde in the reaction vessel. The reaction vessel is sealed and heated to 70° C. for 15 mins to effect conjugation. After cooling to room temperature, the product is obtained by preparative radio HPLC (as described for method 1) or by SPE.

SPECIFIC EMBODIMENTS, CITATION OF REFERENCES

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method of preparing a radiofluorinated compound comprising the steps;

(i) for a compound of formula (I)

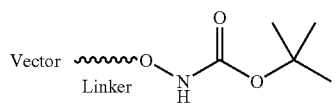

the Boc-protecting group of (I) is removed by irradiating the Boc-protected aminoxy group on a supported material with microwave activation to give a compound of formula (II);

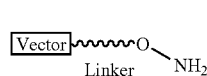

(ii) the compound (II) is reacted with a $^{18}$F-fluoride synthon of formula X—R$^1$-$^{18}$F to prepare the compound of formula (III)

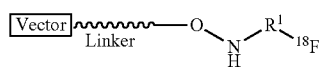

wherein

R$^1$ is alkylene or arylene; wherein when R$^1$ is arylene X is CHO, Hal or OTs and wherein when R$^1$ is alkylene X is CHO or OMs; and wherein step (ii) is also performed on a supported material with microwave activation.

2. A method as claimed in claim 1 wherein the vector is a peptide based vector.

3. A method as claimed in claim 1 wherein the vector is an RGD-based peptide having affinity for angiogenesis.

4. A method as claimed in claim 1 wherein the linker is based on a PEG building block.

5. A method as claimed in claim 1 wherein the $^{18}$F-fluoride synthon is $^{18}$F-radiolabelled benzaldehyde.

6. A method as claimed in claim 1 wherein compound of formula (I) is of formula (IV)

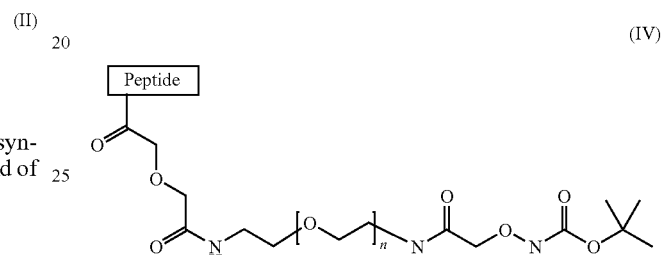

wherein n=3-5 and n is preferably 5.

7. A method as claimed in claim 1 preparing a compound of formula (V)

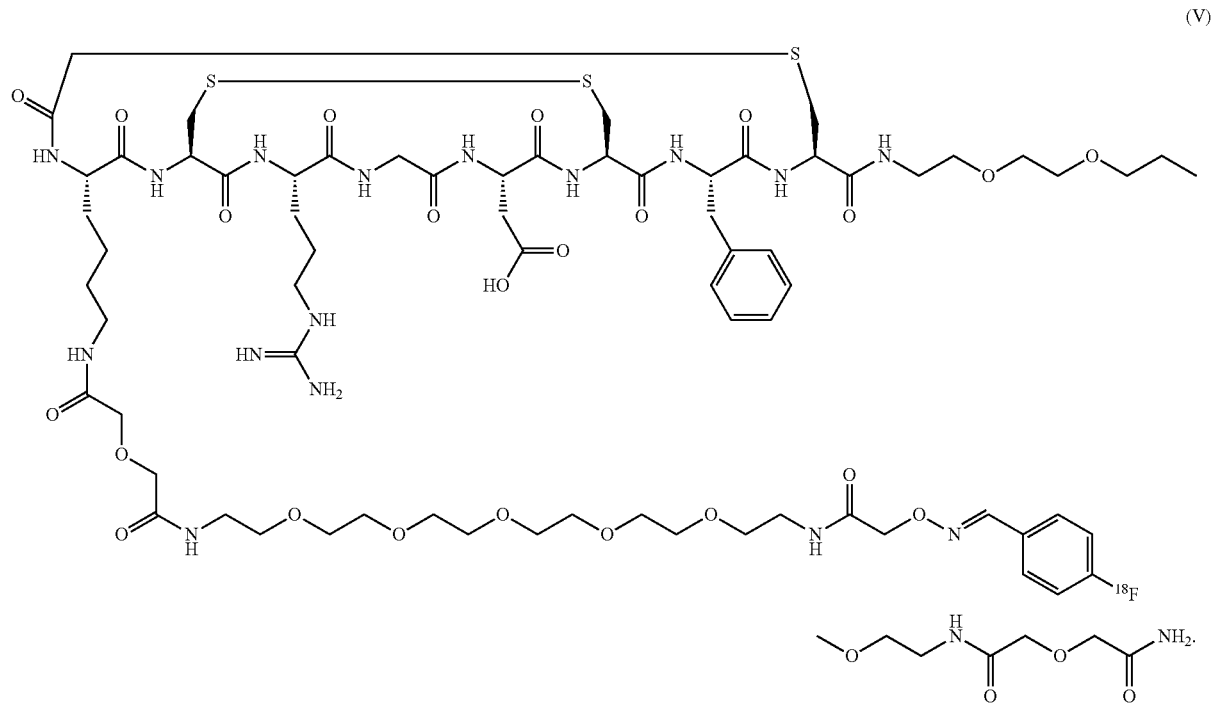

SEQ ID NO: 1.

8. The method according to claim 1, wherein the supported material is silica gel, $SiO_2$, alumina, clay, graphite, $MnO_2$, or solid phase extraction cartridges.

9. A method as claimed in claim 1 wherein the supported material is silica gel.

10. A method for preparing a compound of formula (III) using microwave activation according to claim 1, wherein microwave activation is carried out by a microwave activation system further wherein a reactor vessel is found inside a microwave oven which is connected to an automated radio-synthesis apparatus via elongated tubing.

11. A method for preparing a compound of formula (III) using microwave activation according to claim 9, wherein a reactor vessel is found inside a monomodal microwave oven.

12. A method for preparing a compound of formula (III) using microwave activation according to claim 1, wherein microwave activation is carried out at wavelengths shorter than one meter and longer than one millimeter.

* * * * *

SEQUENCE LISTING

```
<160> NUMBER OF SEQ ID NOS: 4

<210> SEQ ID NO 1
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: -COCH2OCH2CONHCH2[CH2OCH2]5-CH2NH(CO)CH2O-
      N=C-C6H4-18F substituent on the Lys epsilon amine group
<220> FEATURE:
<221> NAME/KEY: THIOETH
<222> LOCATION: (1)..(8)
<220> FEATURE:
<221> NAME/KEY: DISULFID
<222> LOCATION: (2)..(6)
<220> FEATURE:
<221> NAME/KEY: MISC_FEATURE
<222> LOCATION: (8)..(8)
<223> OTHER INFORMATION: -CH2[CH2OCH2]3-CH2NH(CO)-CH2OCH2CONH2
      substituent on the N-terminus

<400> SEQUENCE: 1

Lys Cys Arg Gly Asp Cys Phe Cys
1               5

<210> SEQ ID NO 2
<211> LENGTH: 8
```

```
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: -COCH2OCH2CONHCH2[CH2OCH2]5-CH2NH(CO)CH2-O-
      NH(CO)OC(CH3)3 substituent on the Lys epsilon amine group
<220> FEATURE:
<221> NAME/KEY: THIOETH
<222> LOCATION: (1)..(8)
<220> FEATURE:
<221> NAME/KEY: DISULFID
<222> LOCATION: (2)..(6)
<220> FEATURE:
<221> NAME/KEY: MISC_FEATURE
<222> LOCATION: (8)..(8)
<223> OTHER INFORMATION: -CH2[CH2OCH2]3-CH2NH(CO)-CH2OCH2CONH2
      substituent on the N-terminus

<400> SEQUENCE: 2

Lys Cys Arg Gly Asp Cys Phe Cys
1               5

<210> SEQ ID NO 3
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: -COCH2OCH2CONHCH2[CH2OCH2]5-CH2NH(CO)CH2-O-
      NH2 substituent on the Lys epsilon amine group
<220> FEATURE:
<221> NAME/KEY: THIOETH
<222> LOCATION: (1)..(8)
<220> FEATURE:
<221> NAME/KEY: DISULFID
<222> LOCATION: (2)..(6)
<220> FEATURE:
<221> NAME/KEY: MISC_FEATURE
<222> LOCATION: (8)..(8)
<223> OTHER INFORMATION: -CH2[CH2OCH2]3-CH2NH(CO)-CH2OCH2CONH2
      substituent on the N-terminus

<400> SEQUENCE: 3

Lys Cys Arg Gly Asp Cys Phe Cys
1               5

<210> SEQ ID NO 4
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: THIOETH
<222> LOCATION: (1)..(8)
<220> FEATURE:
<221> NAME/KEY: DISULFID
<222> LOCATION: (2)..(6)
<220> FEATURE:
<221> NAME/KEY: MISC_FEATURE
<222> LOCATION: (8)..(8)
<223> OTHER INFORMATION: -CH2[CH2OCH2]3-CH2NH(CO)-CH2OCH2CONH2
      substituent on the N-terminus

<400> SEQUENCE: 4

Lys Cys Arg Gly Asp Cys Phe Cys
1               5
```